US00PP27099P2

(12) United States Plant Patent
Geerlings

(10) Patent No.: US PP27,099 P2
(45) Date of Patent: Aug. 23, 2016

(54) ***ASTRANTIA* PLANT NAMED 'PISA'**

(50) Latin Name: *Astrantia major*
Varietal Denomination: Pisa

(71) Applicant: El Geerlings, Lisserbroek (NL)

(72) Inventor: El Geerlings, Lisserbroek (NL)

(73) Assignee: Green Elik Collection B.V., Lisserbroek (NL)

( * ) Notice: Subject to any disclaimer, the term of this patent is extended or adjusted under 35 U.S.C. 154(b) by 67 days.

(21) Appl. No.: 14/121,892

(22) Filed: Oct. 31, 2014

(51) Int. Cl.
*A01H 5/02* (2006.01)

(52) U.S. Cl.
USPC ..... Plt./408

(58) Field of Classification Search
USPC ..... Plt./408
See application file for complete search history.

*Primary Examiner* — Anne Grunberg
(74) *Attorney, Agent, or Firm* — C. A. Whealy

(57) ABSTRACT

A new and distinct cultivar of *Astrantia* plant named 'Pisa', characterized by its upright plant habit with long flowering stems; freely-branching habit; freely and continuous flowering habit; long flowering period; inflorescences with showy involucral bracts that are white in color; and good garden performance.

3 Drawing Sheets

Botanical designation: *Astrantia major.*
Cultivar denomination: 'PISA'.

BACKGROUND OF THE INVENTION

The present invention relates to a new and distinct *Astrantia* plant, botanically known as *Astrantia major* and hereinafter referred to by the name 'Pisa'.

The new *Astrantia* plant is a product of a planned breeding program conducted by the Inventor in Lisserbroek, The Netherlands. The objective of the breeding program is to create new freely branching *Astrantia* plants with large and attractive flowers.

The new *Astrantia* plant originated from a self-pollination during the summer of 2011 of *Astrantia major* 'Snow Star', disclosed in U.S. Plant Pat. No. 12,697. The new *Astrantia* plant was discovered and selected by the Inventor as a single flowering plant from within the progeny of the stated self-pollination grown in a controlled environment in Lisserbroek, The Netherlands during the summer of 2012.

Asexual reproduction of the new *Astrantia* plant by divisions in Lisserbroek, The Netherlands since 2014 has shown that the unique features of this new *Astrantia* plant are stable and reproduced true to type in successive generations.

SUMMARY OF THE INVENTION

Plants of the new *Astrantia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pisa'. These characteristics in combination distinguish 'Pisa' as a new and distinct *Astrantia* plant:

1. Upright plant habit with long flowering stems.
2. Freely-branching habit.

3. Freely and continuous flowering habit; long flowering period.
4. Inflorescences with showy involucral bracts that are white in color.
5. Good garden performance.

Plants of the new *Astrantia* differ from plants of the parent, 'Snow Star', primarily in the following characteristics:

1. Plants of the new *Astrantia* are more freely-branching than plants of 'Snow Star'.
2. Plants of the new *Astrantia* have larger inflorescences than plants of 'Snow Star'.
3. Inflorescences of plants of the new *Astrantia* have longer postproduction longevity than inflorescences of plants of 'Snow Star'.

Plants of the new *Astrantia* can be compared to plants of *Astrantia major* 'Alba', not patented. In side-by-side comparisons conducted by the Inventor in Lisserbroek, The Netherlands, plants of the new *Astrantia* differed primarily from plants of 'Alba' in the following characteristics:

1. Plants of the new *Astrantia* were more freely-branching than plants of 'Alba'.
2. Plants of the new *Astrantia* had longer flowering stems than plants of 'Alba'.
3. Plants of the new *Astrantia* had larger inflorescences than plants of 'Alba'.

Plants of the new *Astrantia* can also be compared to plants of *Astrantia major* 'Shaggy', not patented. In side-by-side comparisons conducted by the Inventor in Lisserbroek, The Netherlands, plants of the new *Astrantia* differed primarily from plants of 'Shaggy' in the following characteristics:

1. Plants of the new *Astrantia* were more freely-branching than plants of 'Shaggy'.
2. Plants of the new *Astrantia* had longer flowering stems than plants of 'Shaggy'.
3. Plants of the new *Astrantia* and 'Shaggy' differed slightly in involucral bract coloration.

BRIEF DESCRIPTION OF THE PHOTOGRAPHS

The accompanying colored photographs illustrate the overall appearance of the new *Astrantia* plant showing the colors as true as it is reasonably possible to obtain in colored reproductions of this type. Colors in the photographs may differ slightly from the color values cited in the detailed botanical description which accurately describe the actual colors of the new *Astrantia* plant.

The photograph on the first sheet is a side perspective view of a typical flowering plant of 'Pisa' grown in a container.

The photograph on the second sheet is a close-up view of typical leaves of 'Pisa'.

The photograph on the third sheet is a close-up view of typical flowering stems of 'Pisa'.

DETAILED BOTANICAL DESCRIPTION

Plants used for the aforementioned photographs and the following description were grown during the summer and early autumn in an outdoor nursery in Lisserbroek, The Netherlands and under cultural practices typical of commercial *Astrantia* production. During the production of the plants, day temperatures ranged from 15° C. to 30° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Astrantia major* cultivar Pisa.

Parentage: Self-pollination of *Astrantia major* 'Snow Star', disclosed in U.S. Plant Pat. No. 12,697.

Propagation:

*Type*.—By divisions.

*Time to initiate roots, summer*.—About one month at air temperatures about 15° to 18° C.

*Time to produce a rooted young plant, summer*.—About four months at air temperatures about 15° to 18° C.

*Root description*.—Fine, fibrous; coppery brown in color.

*Rooting habit*.—Freely branching; dense.

Plant description:

*Plant and growth habit*.—Upright perennial flowering plant with basal rosette of leaves; numerous erect peduncles support umbels of flowers held well above the foliar plane; moderately vigorous growth habit.

*Plant height, soil level to top of inflorescences*.—About 56 cm.

*Plant height, soil level to top of foliar plane*.—About 23.8 cm.

*Plant width*.—About 40.3 cm.

*Flowering stem description*.—Arrangement: Branching mostly basal; freely branching, about numerous flowering stems developing per plant during the growing season. Length: About 48.6 cm. Diameter: About 3 mm. Internode length: About 18.5 cm. Strength: Strong. Aspect: Upright to 30° from vertical. Texture: Smooth, glabrous. Color: Close to 144A to 144B.

Leaf description:

*Arrangement*.—Alternate, simple.

*Length, basal leaves*.—About 9.9 cm.

*Length, stem leaves*.—About 5.4 cm.

*Width, basal leaves*.—About 11.5 cm.

*Width, stem leaves*.—About 5.6 cm.

*Shape*.—Palmately-lobed.

*Apex*.—Acute.

*Base*.—Hastate.

*Margin*.—Biserrate.

*Texture, upper and lower surfaces*.—Slightly rugose, glabrous.

*Venation pattern*.—Pinnate.

*Color*.—Developing leaves, upper surface: Close to 144A. Developing leaves, lower surface: Close to 143C. Fully expanded leaves, upper surface: Close to between 137B and 146A; venation, close to between 137B and 146A. Fully expanded leaves, lower surface: Close to 138B; venation, close to 144B.

*Petiole length, basal leaves*.—About 19.1 cm.

*Petiole length, stem leaves*.—About 3.2 cm.

*Petiole diameter, basal leaves*.—About 2 mm to 3 mm.

*Petiole diameter, stem leaves*.—About 1 mm.

*Petiole color, basal leaves, upper and lower surfaces*.—Close to 144A.

*Petiole color, stem leaves, upper and lower surfaces*.—Close to 143A and 144A.

Inflorescence description:

*Flower arrangement and appearance*.—Numerous, single, minute campanulate flowers subtended by showy involucral bracts; flowers arrange in compound umbels; flowers face mostly upright to somewhat outwardly; freely flowering habit with typically about 60 flowers developing per umbel and about nine umbels developing per flowering stem.

*Natural flowering season*.—Long flowering season, flowering continuous from late spring to late summer in The Netherlands; plants begin flowering about nine months after planting.

*Flower longevity on the plant*.—About twelve days; flowers not persistent.

*Fragrance*.—Moderate.

*Flower buds*.—Length: About 2 mm. Diameter: About 2 mm. Shape: Obovate with flattened apex. Color: Close to 143C; towards the apex, close to NN155A.

*Inflorescence height*.—About 1.8 cm.

*Inflorescence diameter*.—About 3.3 cm.

*Flower diameter*.—About 4 mm.

*Flower depth (height)*.—About 5 mm.

*Petals*.—Arrangement: Five in a single whorl. Length: About 2 mm. Width: About 0.75 mm. Shape: Narrowly elliptic; recurved. Apex: Narrowly acute. Margin: Entire. Texture, upper and lower surfaces: Smooth, glabrous. Color: When opening, upper and lower surfaces: Close to NN155A. Fully opened, upper and lower surfaces: Close to NN155C.

*Sepals*.—Arrangement: Five in a single whorl. Length: About 1 mm. Width: About 0.8 mm. Shape: Ovate. Apex: Acute. Base: Cuneate. Margin: Entire. Texture, upper and lower surfaces: Smooth, glabrous. Color: When opening, upper and lower surfaces: Close to 143A. Fully opened, upper and lower surfaces: Close to 143A.

*Involucral bracts*.—Arrangement: About 15 in a single whorl. Length: About 1.6 cm. Width: About 4.5 mm. Shape: Obovate. Apex: Acute. Base: Attenuate. Margin: Entire. Texture, upper and lower surfaces: Smooth, glabrous. Color, when opening and fully opened, upper and lower surfaces: Close to NN155A; towards the base, close to 143B; venation, close to 143B.

*Peduncles*.—Length: About 5.3 cm. Diameter: About 1.5 mm. Strength: Strong. Aspect: Upright to about 35° from vertical. Texture: Smooth, glabrous. Color: Close to 143A.

*Pedicels*.—Length: About 9 mm. Diameter: About 0.2 mm. Strength: Strong. Aspect: Erect to about 80° from vertical. Texture: Smooth, glabrous. Color: Close to N155B.

*Reproductive organs*.—Stamens: Quantity per flower: Five. Filament length: About 3.5 mm. Anther shape: Double reniform. Anther length: About 0.75 mm. Anther color: Close to N77B. Pollen amount: Scarce. Pollen color: Close to 156D. Pistils: Quantity per flower: Two. Pistil length: About 4 mm. Stigma shape: Club-shaped. Stigma color: Close to NN155B. Style length: About 3.8 mm. Style color: Close to NN155C to NN155D. Ovary color: Close to 143A; ribs, close to 157D.

*Seeds and fruits*.—Seed and fruit production has not been observed on plants of the new *Astrantia*.

Disease & pest resistance: Plants of the new *Astrantia* have not been noted to be resistant to pathogens and pests common to *Astrantia* plants.

Garden performance: Plants of the new *Astrantia* have exhibited good tolerance to rain, wind and high temperatures about 35° C. and to be hardy to USDA Hardiness Zone 5.

It is claimed:

1. A new and distinct *Astrantia* plant named 'Pisa' as illustrated and described.

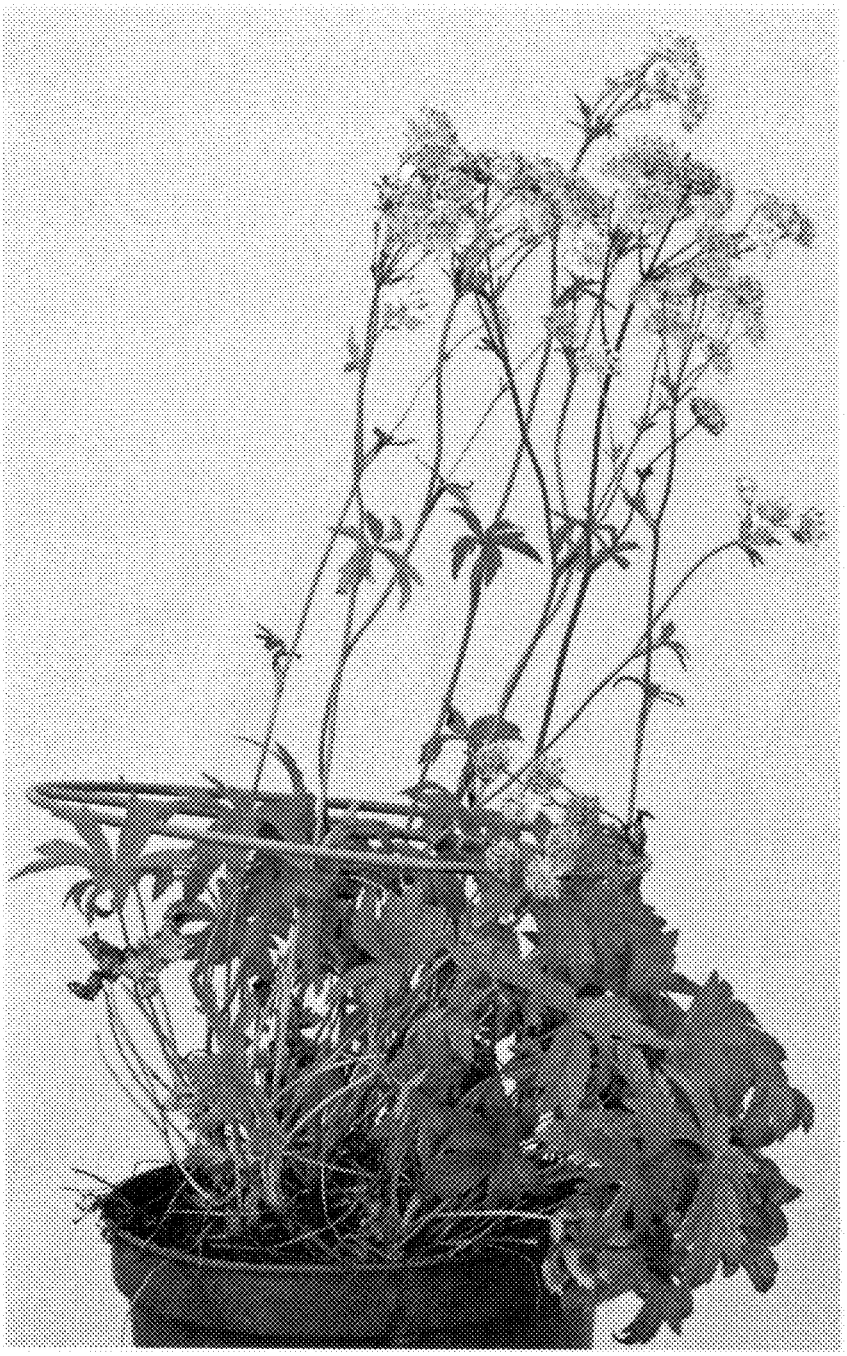

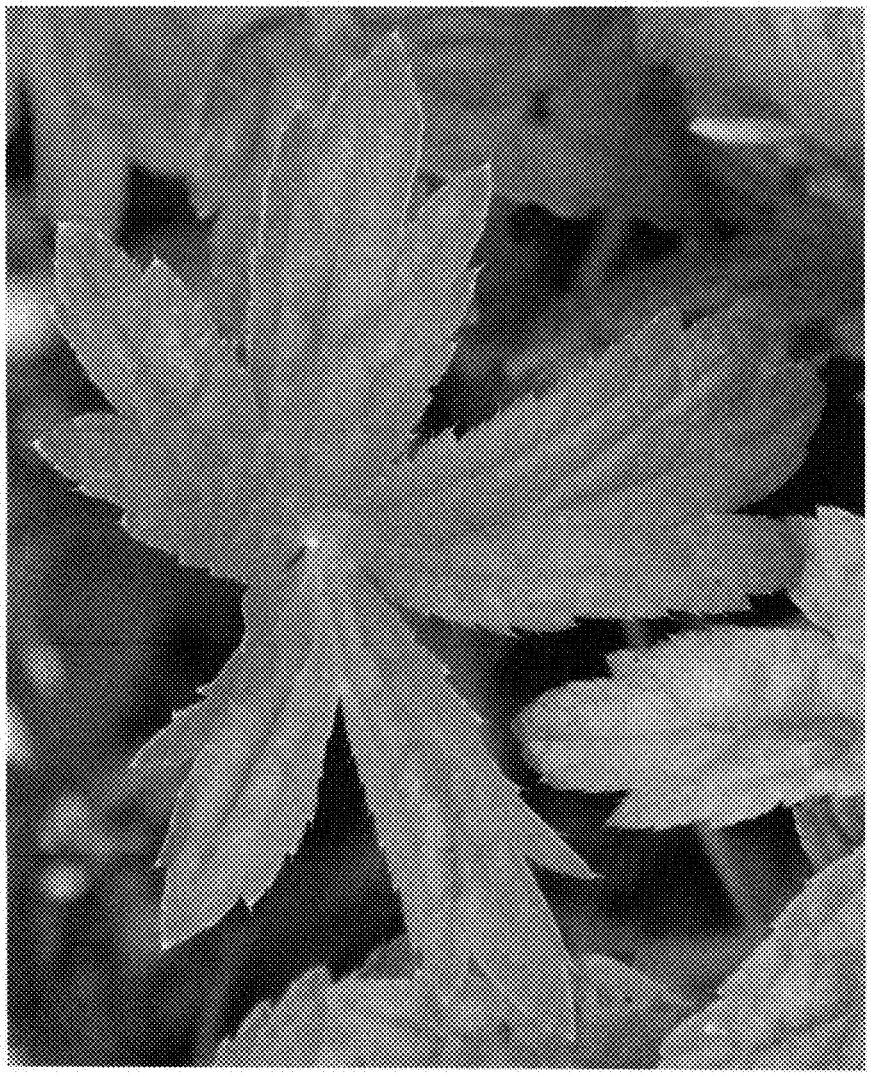

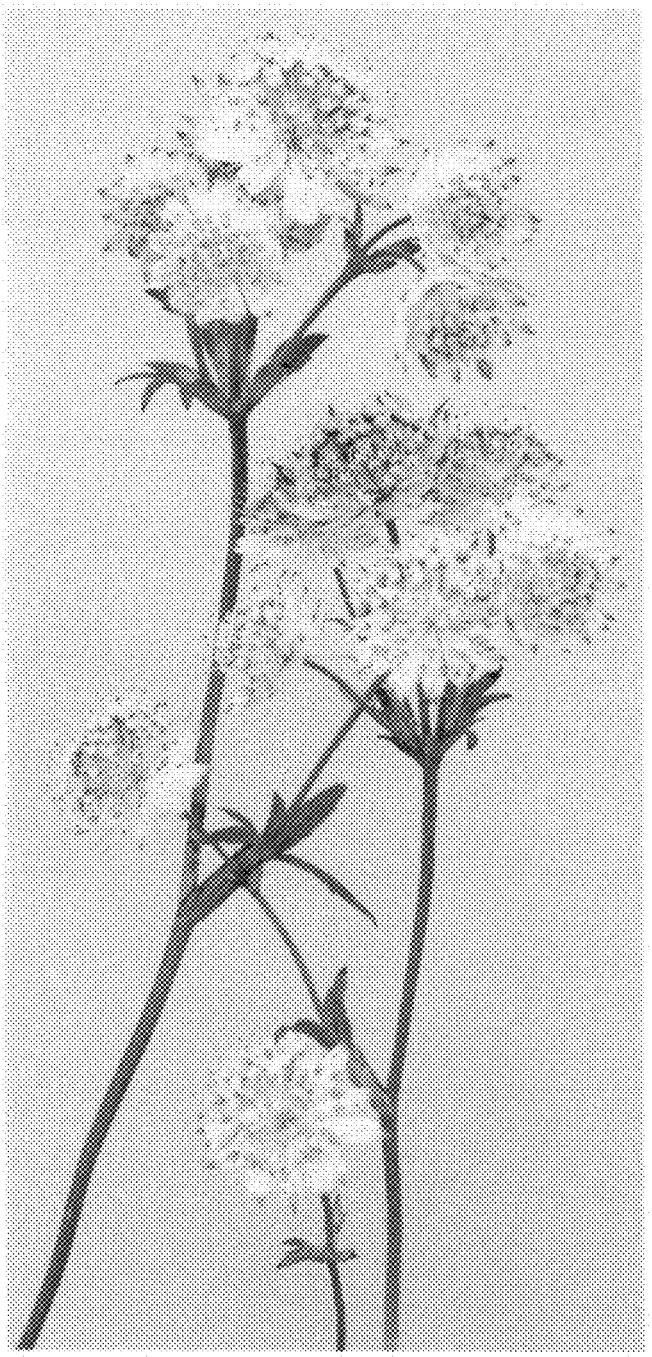

* * * * *